United States Patent [19]

Timmons et al.

[11] Patent Number: 4,708,446
[45] Date of Patent: * Nov. 24, 1987

[54] EYEGLASS FRAME AND NASAL CANNULA ASSEMBLY

[75] Inventors: John W. Timmons; Gloria A. Timmons, both of Sarasota, Fla.

[73] Assignee: Engineered Specialty Products, Sarasota, Fla.

[ * ] Notice: The portion of the term of this patent subsequent to Dec. 24, 2002 has been disclaimed.

[21] Appl. No.: 808,615

[22] Filed: Dec. 13, 1985

[51] Int. Cl.$^4$ ............................ G02C 1/00; A62B 9/06
[52] U.S. Cl. ................................. 351/158; 128/207.18
[58] Field of Search .................... 351/158, 41, 124; 128/207.18, 204.12, 206.18, 201.12, 207.13

[56] References Cited

U.S. PATENT DOCUMENTS 2,168,705  8/1939  Francisco .
2,468,383  4/1949  Tiffany .

Primary Examiner—Rodney B. Bovernick
Attorney, Agent, or Firm—Charles J. Prescott

[57] ABSTRACT

An improved eyeglass frame and nasal cannula assembly for inconspicuously administering oxygen or other gases into the nostrils of a patient having respiratory ailments. The eyeglass frame has a pair of grooves in the rear surface of its front piece and a groove in the interior surface of each of its hinged temples. The nasal cannula assembly includes a pair of cannula tubes fitted in these grooves. The nasal portion of each of the cannula tubes is adapted for insertion in one nostril of the patient's nose while the end of the free portion of each cannula tube is connectable to a portable or stationary source of oxygen or other gas to be administered to the patient. The lower end of the nasal portion is adapted for retention in the use's nostril by a gentle gripping action of the ala of the nostril and also shaped for improved functioning and comfort. The entire nasal portion of the cannula tube, including the shaped lower end, is replaceable. To improve comfort and retention of the lower end of the cannula tube in the user's nostril, the groove in the nosepiece of the eyeglass frame is shaped to redirect the lower end of the cannula tube downwardly and inwardly toward the nostril. The overall appearance of the eyeglass frame is substantially identical to that of a conventional eyeglass frame and all but a small portion of the cannula tubes are hidden from view.

28 Claims, 4 Drawing Figures

EYEGLASS FRAME AND NASAL CANNULA ASSEMBLY

BACKGROUND OF THE INVENTION

This invention relates generally to the administering of oxygen or other gases to a patient having respiratory ailments, and more particularly to improvements in an eyeglass frame and nasal cannula assembly for incospicuously administering such gases comfortably into the nostrils of such a patient.

Certain respiratory ailments require the administering of oxygen or other gases to a patient over an extended period of time. Nasal cannula assemblies for administering oxygen or other gases to a patient having such respiratory ailments are well known in the prior art. However, the use of prior art nasal cannula asemblies in public can be embarrassing to many patients. Accordingly, many ambulatory patients who would otherwise be capable of dining in restaurants, attending plays, movies or sports events, visiting friends or relatives or otherwise participating in activities away from their homes will often confine themselves to their homes to avoid embarrassment.

Notwithstanding numerous developments relating to nasal cannula assemblies, it is not believed that the prior art provides a nasal cannula assembly for inconspicuously administering oxygen or other gases into the nostrils of a patient having respiratory ailments. Furthermore, it is not believed that the prior art provides an eyeglass frame and nasal cannula assembly other than applicant's prior invention discussed below. Yet, an eyeglass frame and nasal cannula assembly could be used for inconspicuously administering oxygen or other gases into the nostrils of a patient having respiratory ailments. Further, no references are known in conjunction with eyeglass frames for delivery of oxygen through a nasal cannula having a replaceable nasal portion.

Applicants also cite their soon to be issued U.S. Pat. No. 4,559,941 having an issue date of Dec. 24, 1985 in which is disclosed and claimed the basic eyeglass frame and cannula assembly structure upon which the present invention is an improvement.

SUMMARY OF THE INVENTION

The present invention is directed to an improved eyeglass frame and nasal cannula assembly for inconspicuously administering oxygen or other gases into the nostrils of a patient having respiratory ailments. The eyeglass frame has a pair of grooves in the rear surface of its front piece and a groove in the interior surface of each of its hinged temples. The nasal cannula assembly includes a pair of cannula tubes fitted in these grooves. The nasal portion of each of the cannula tubes is adapted for insertion in one nostril of the patient's nose while the end of the free portion of each cannula tube is connectable to a portable or stationary source of oxygen or other gas to be administered to the patient. The lower end of the nasal portion is shaped for retention in the user's nostril by a gentle gripping action of the ala of the nostril and also shaped for improved functioning and comfort. The entire nasal portion of the cannula tube, including the shaped lower end is replaceable. To improve comfort and retention of the lower end of the cannula tube in the user's nostril, the groove in the nosepiece of the eyeglass frame is shaped to redirect the lower end of the cannula tube downwardly and inwardly toward the nostril. The overall appearance of the eyeglass frame is substantially identical to that of a conventional eyeglass frame and all but a small portion of the cannula tubes are hidden from view.

It is therefore an object of this invention to provide an improved eyeglass frame and nasal cannula assembly for both inconspicuous administration of oxygen or other gases into the nostrils of a patient having respiratory ailments and for improved retention, comfort, and functioning of the lower end of the nasal portion of each cannula tube in relation to the user's nostrils.

It is another object to provide the above invention having the nasal portion of each cannula tube which interacts with the user's nostrils replaceable.

It is yet another object of the above invention to provide improved groove structure in the nosepiece of the eyeglass frame for retaining and redirecting the nasal portion of the cannula tube toward the user's nostril for further increased comfort and retention.

In accordance with these and other objects which will become apparent hereinafter, the instant invention will now be described with reference to the accompanying drawings in which:

DETAILED DESCRIPTION OF THE INVENTION

Figure 1:
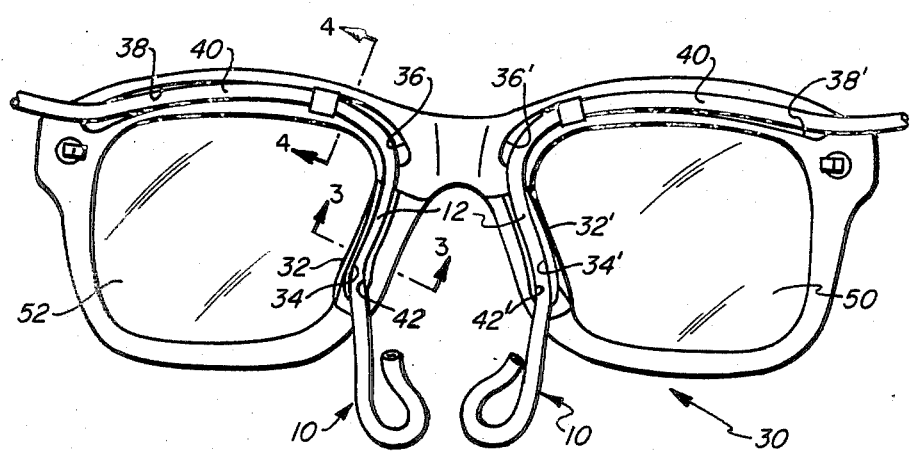
FIG. 1 is a rear elevation view of the improved eyeglass frame and nasal cannula assembly with the temples of the eyeglasses removed.
Figure 2:
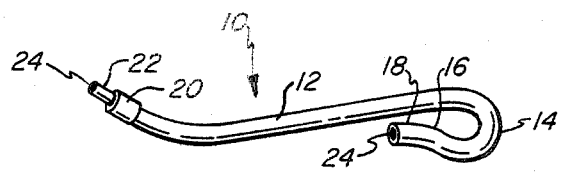
FIG. 2 is a perspective view of the replaceable nasal portion of the cannula tube.

Referring now to the drawings, and particularly to FIGS. 1 and 2, the front piece of the eyeglass frame is shown generally at 30 and is depicted with the hinged temples removed. The general appearance of the eyeglass frame and front piece 30 is substantially identical to that of a typical conventional plastic eyeglass frame and may be varied to accommodate style change and preferences. For example, various masculine and feminine models can be provided in a product line. Additionally, prescription lenses can be used with the eyeglass frame if desired.

The front piece 30 includes lenses 50 and 52 secured therein and having a center bridge portion integrally formed with the portions of the front piece 30 which surround the lenses 50 and 52. Although not shown, each of the temples has an essentially straight, elongated portion which extends rearward from the front piece along the side of the user's face and a downwardly curved portion which fits behind the user's ear to retain the eyeglass frame in position for use. Each of the temples is connected to the front piece by a hinge positioned near the outer margins of the front piece as shown and connected in a well known manner.

The rear surface of the front piece 30 shown in FIG. 1 has an identical pair of grooves each including groove portion 38 and 38' above the lens, enlarged groove portions 36 and 36' at the upper inner corners of the lenses adjacent the bridge, and nose piece groove portions 34 and 34' which are within or adjacent the nose piece 32 and 32'.

Each cannula assembly includes a replaceable nasal portion 10 best seen in FIG. 2, a mid-portion 40, and a free portion (not shown). The mid-portion 40 interconnects to the connector portion 22 of the nasal portion 10 in FIG. 2 and extends rearwardly along the length of the grooved temples and are connectable to a small bottle or other portable or stationary source of oxygen or other gas to be administered to the user into his nostrils. If desired, a portable or stationary source of oxygen can be concealed from view under a coat or other similar item of the user's clothing.

The replaceable nasal portion 10, shown best in FIG. 2, includes an elongated main tubular portion 12, a reduced-diameter connector portion 22 at one end with an adjacent enlarged-diameter collar 20 to assist in assembly to the mid-portion 40 of the cannula assembly. The lower end of the replaceable nasal portion 10 includes a curved portion 14 bending through more than 180 degrees of curvature as shown followed by a recurve or reverse bend at 16 and a relative straight portion 18 at the distal end. Gases pass through the inner passage 24 discharging at distal end portion 18 into the user's nostrils.

An important aspect of the contour depicted at the lower end of the replaceable nasal tube 10 is that it will not only introduce oxygen into the user's nostril, but will also gently grip the ala of the nostril by the spring bias action created by this unique contour. Because the material is fabricated of relatively soft and pliable plastic material, this gripping action produces a relatively comfortable positioning force on the ala of the nostril.

There are other important functional aspects of this unique shape in the lower end of the nasal portion 10. As curved portion 14 is opened somewhat to increase the gap between 16 and the opposing tube portion to accommodate the tissue thickness of the ala, straight portion 18 becomes angled away from the inner tissue surface of the ala. This also insures that the distal end cannot contact the inner surface tissue. Therefore by this means, no tissure irritation is caused by contact with the harsh distal end, the flow of oxygen is better directed into the nostril for use, and mucus will be far less likely to collect in and block the distal end.

Another important aspect of this invention is the contour of the nosepiece groove portions 34 and 34' of the nosepiece 32 and 32' at 42. As seen in FIG. 1, this nosepiece groove portion 34 and 34' is contoured and shaped so as to redirect the lower ends of the replaceable nasal portion 10 downwardly and inwardly toward the user's nostrils. By this means, virtually all of the natural spring bias action of the main elongated portion 12 which tends to pull the lower end contour portion away from the nostrils is eliminated. These lower end portions of the replaceable nasal portion 10 are thereby positioned precisely for comfortable, untensioned insertion into the user's nostrils, regardless of the breadth of nose. These nosepiece groove portions 34 and 34' are also easily adapted in shape at 42 and 42' so as to provide a custom and precise fit for each user.

Figure 3:
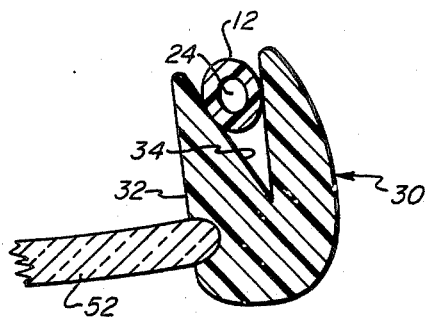
FIG. 3 is a section view in the direction of arrows 3-3 in FIG. 1.

Referring to FIG. 3, the nosepiece groove 34 in the nosepiece 32 is wedge-shaped so that, as the mid-portion 12 is squeezeably inserted therein wedging action retains the mid-portion 12 therein.

Figure 4:
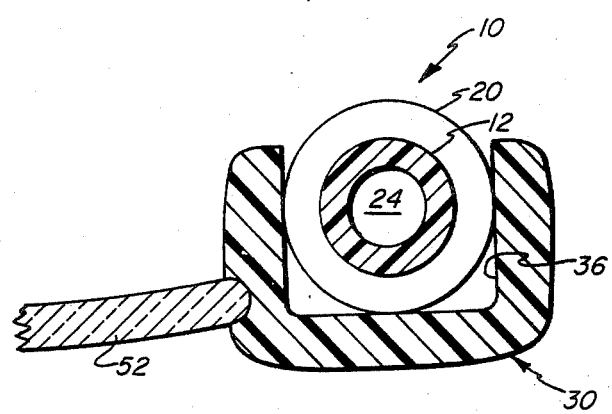
FIG. 4 is a section view in the direction of arrows 4-4 in FIG. 1.

Referring to FIG. 4, the enlarged mid-portion 36 and 36' of the front piece grooves are provided so that the assembly-assisting enlarged collar 20 may be received for concealment to the same degree as the rest of the cannula tube.

While the instant invention has been shown and described herein in what is conceived to be the most practical and preferred embodiment, it is recognized that departures may be made therefrom within the scope of the invention, which is therefore not to be limited to the details disclosed herein, but is to be accorded the full scope of the claims so as to embrace any and all equivalent and articles.

What is claimed is:

1. In an eyeglass frame with a concealed nasal cannula assembly, said eyeglass frame having a front piece and a pair of hinged temples, said front piece having a groove in its rear surface for receiving the mid-portion of said cannula assembly, the improvement comprising:

shaped means integrally formed in the lower end of the nasal portion of said cannula assembly for retaining said lower end in the user's nostril by gentle spring biased griping of the ala of the nostril.

2. An eyeglass frame with a concealed nasal cannula assembly as set forth in claim 1, wherein:

said shaped means is also for improved oxygen delivery into the user's nostril.

3. An eyeglass frame with a concealed nasal cannula assembly as set forth in claim 1, wherein:

said shaped means is also for preventing irritating contact between the distal end of said nasal portion and the inner surface of the nostril.

4. An eyeglass frame with a concealed nasal cannula assembly as set forth in claim 1, wherein:

said shaped means is also for preventing mucus buildup in the distal end of said nasal portion.

5. An eyeglass frame with a concealed nasal cannula assembly as set forth in claim 1, wherein:

said shaped means includes a bend in said lower end of said nasal portion through more than 180 degrees followed by a reverse bend such that said distal end is disposed generally parallel to and in the opposite direction to the straight portion of said nasal portion.

6. An eyeglass frame with a concealed nasal cannula assembly as set forth in claim 1, wherein:

said nasal portion is separate and replaceable and connectable to the mid-portion of said cannula assembly;

said groove is adapted to also receive the connector between said nasal portion and said cannula assembly.

7. An eyeglass frame with a concealed nasal cannula assembly as set forth in claim 1, wherein:

the portion of said groove in the nosepiece of said front piece is shaped to direct said lower end of said nasal portion inwardly toward the ala of the user's nostril whereby retention, user comfort, and unobstrusiveness of said nasal portion are enhanced.

8. An eyeglass frame with a concealed nasal cannula assembly as set forth in claim 7, wherein:

said portion of said groove in said nosepiece has a V-shaped cross section for releasable retention of said nasal portion.

9. An eyeglass frame with a concealed nasal cannula assembly as set forth in claim 2, wherein:

said shaped means is also for preventing irritating contact between the distal end of said nasal portion and the inner surface of the nostril;

said shaped means is also for preventing mucus buildup in said distal end of said nasal portion;

said shaped means includes a bend in said lower end of said nasal portion through more than 180 degrees followed by a reverse bend such that said distal end is disposed generally parallel to and in the opposite direction to the straight portion of said nasal portion;

said nasal portion is separate and replaceable and connectable to said cannula assembly;

said groove adapted to also receive the connector between said nasal portion and said cannula assembly;

the portion of said groove in the nosepiece of said front piece shaped to direct said lower end of said nasal portion inwardly toward the ala of the user's nostril whereby retention, user comfort, and unobtrusiveness of said nasal portion are enhanced;

said portion of said groove in said nosepiece has a V-shaped cross section for releaseable retention of said nasal portion.

10. An improved eyeglass frame with a concealed nasal cannula assembly comprising:

an eyeglass frame having a front piece and a pair of hinged temples, said front piece having a pair of lens surrounding and retaining members separated by an integrally formed bridge, each of said lens surrounding and retaining members having an integrally formed nosepiece, and a pair of grooves in its rear surface, each of said grooves commencing near one of said hinged temples, following the contour of the upper portion of one of said lens surrounding and retaining members, running through said bridge, running between one of said nosepieces and the lens opening of one of said lens surrounding and retaining members, and terminating below said nosepieces;

a pair of identical cannula tubes, each of cannula tubes having shaped means integrally formed in the lower end of said cannula tube for retaining said lower end in the user's nostril by gentle spring-biased gripping of the ala of the nostril, and each of said cannula tubes being fitted in one of said grooves in the rear surface of said front piece whereby the portions of said cannula tubes fitted into said grooves are concealed.

11. In an eyeglass frame with a concealed nasal cannula assembly including a pair of identical cannula tubes, said eyeglass frame having a front piece and a pair of hinged temples, said front piece having a pair of grooves in its rear surface each for receiving the mid-portion of one said cannula tube, the improvement comprising:

shaped means integrally formed in the lower end of the nasal portion of said cannula tube for retaining said lower end in the user's nostril by gentle spring biased gripping of the ala of the nostril.

12. An eyeglass frame with a concealed nasal cannula assembly as set forth in claim 11, wherein:

said shaped means is also for improved oxygen delivery into the user's nostril.

13. An eyeglass frame with a concealed nasal cannula assembly as set forth in claim 11, wherein:

said shaped means is also for preventing irritating contact between the distal end of said nasal portion and the inner surface of the nostril.

14. An eyeglass frame with a concealed nasal cannula assembly as set forth in claim 11, wherein:

said shaped means is also for preventing mucus buildup in the distal end of said nasal portion.

15. An eyeglass frame with a concealed nasal cannula assembly as set forth in claim 11, wherein:

said shaped means includes a bend in said lower end of said nasal portion through more than 180 degrees followed by a reverse bend such that said distal end is disposed generally parallel to and in the opposite direction to the straight portion of said nasal portion.

16. An eyeglass frame with a concealed nasal cannula assembly as set forth in claim 11, wherein:

said nasal portion is separate and replaceable and connectable by a connector to the mid-portion of said cannula tube;

said groove is adapted to also receive the connector between said nasal portion and said mid-portion of said cannula tubes.

17. An eyeglass frame with a concealed nasal cannula assembly as set forth in claim 11, wherein:

the portion of said groove in the nosepiece of said front piece is shaped to direct said lower end of said nasal portion inwardly toward the ala of the user's nostril whereby retention, user comfort, and unobtrusiveness of said nasal portion are enhanced.

18. An eyeglass frame with a concealed nasal cannula assembly as set forth in claim 7, wherein:

said portion of said groove in said nosepiece has a V-shaped cross section for releaseable retention of said nasal portion.

19. An eyeglass frame with a concealed nasal cannula assembly as set forth in claim 12, wherein:

said shaped means is also for preventing irritating contact between the distal end of said nasal portion and the inner surface of the nostril;

said shaped means is also for preventing mucus buildup in said distal end of said nasal portion;

said shaped means includes a bend in said lower end of said nasal portion through more than 180 degrees followed by a reverse bend such that said distal end is disposed generally parallel to and in the opposite direction to the straight portion of said nasal portion;

said nasal portion is separate and replaceable and connectable to said cannula assembly;

said groove adapted to also receive the connector between said nasal portion and said cannula assembly;

the portion of said groove in the nosepiece of said front piece shaped to direct said lower end of said nasal portion inwardly toward the ala of the user's nostril whereby retention, user comfort, and unobtrusiveness of said nasal portion are enhanced;

said portion of said groove in said nosepiece has a V-shaped cross section for releaseable retention of said nasal portion.

20. An eyeglass frame with a concealed nasal cannula assembly as set forth in claim 1, wherein:

said shaped means includes a bend in said lower end of said nasal portion through more than 180 degrees followed by a reverse bend such that said distal end is generally directed away from the inside surface of the ala and toward the center of the user's nostril when said cannula assembly is installed for use. and in the opposite direction to the straight portion of said nasal portion.

21. An eyeglass frame with a concealed nasal cannula assembly as set forth in claim 11, wherein:

said shaped means includes a bend in said lower end of said nasal portion through more than 180 degrees followed by a reverse bend such that said distal end is generally directed away from the inside surface of the ala and toward the center of the user's nostril when said cannula assembly is installed for use, and in the opposite direction to the straight portion of said nasal portion.

22. In an eyeglass frame with a concealed nasal cannula assembly, said eyeglass frame having a front piece and a pair of hinged temples, said front piece having a groove in its rear surface for receiving the mid-portion of said cannula assembly, the improvement comprising:

a replacable nasal portion having an elongated flexible tubular portion adapted at its first end to be connectable to the main portion of the cannula assembly;

shaped means integrally formed in the lower second end of said nasal portion for retaining said lower end in the user's nostril by gentle spring biased gripping of the ala of the nostril.

23. An eyeglass frame with a concealed nasal cannula assembly as set forth in claim 22, wherein:

said shaped means is also for improved oxygen delivery into the user's nostril.

24. An eyeglass frame with a concealed nasal cannula assembly as set forth in claim 22, wherein:

said shaped means is also for preventing irritating contact between the distal end of said nasal portion and the inner surface of the nostril.

25. An eyeglass frame with a concealed nasal cannula assembly as set forth in claim 22, wherein:

said shaped means is also for preventing mucus buildup in the distal end of said nasal portion.

26. An eyeglass frame with a concealed nasal cannula assembly as set forth in claim 22, wherein:

said shaped means includes a bend in said lower end of said nasal portion through more than 180 degrees followed by a reverse bend such that said distal end is disposed generally parallel to and in the opposite direction to the straight portion of said nasal portion.

27. An eyeglass frame with a concealed nasal cannula assembly as set forth in claim 23, wherein:

said shaped means is also for preventing irritating contact between the distal end of said nasal portion and the inner surface of the nostril;

said shaped means is also for preventing mucus buildup in said distal end of said nasal portion;

said shaped means includes a bend in said lower end of said nasal portion through more than 180 degrees followed by a reverse bend such that said distal end is disposed generally parallel to and in the opposite direction to the straight portion of said nasal portion;

said nasal portion is separate and replaceable and connectable to said cannula assembly;

said groove adapted to also receive the connector between said nasal portion and said cannula assembly;

the portion of said groove in the nosepiece of said front piece shaped to direct said lower end of said nasal portion inwardly toward the ala of the user's nostril whereby retention, user comfort, and unobtrusiveness of said nasal portion are enhanced;

28. An eyeglass frame with a concealed nasal cannula assembly as set forth in claim 22, wherein:

said shaped means includes a bend in said lower end of said nasal portion through more than 180 degrees followed by a reverse bend such that said distal end is generally directed away from the inside surface of the ala and toward the center of the user's nostril when said cannula assembly is installed for use.

* * * * *